United States Patent
Lee et al.

(10) Patent No.: US 11,224,870 B2
(45) Date of Patent: Jan. 18, 2022

(54) LIGAND, OLIGOMERIZATION CATALYST COMPRISING SAME, AND METHOD FOR PRODUCING ETHYLENE OLIGOMER BY USING OLIGOMERIZATION CATALYST

(71) Applicants: SK Innovation Co., Ltd., Seoul (KR); SK Global Chemical Co., Ltd., Seoul (KR)

(72) Inventors: Hoseong Lee, Daejeon (KR); Yongnam Joe, Daejeon (KR)

(73) Assignees: SK Innovation Co., Ltd., Seoul (KR); SK Global Chemical Co., Ltd., Seoul (KR)

(*) Notice: Subject to any disclaimer, the term of this patent is extended or adjusted under 35 U.S.C. 154(b) by 79 days.

(21) Appl. No.: 16/771,857

(22) PCT Filed: Oct. 12, 2018

(86) PCT No.: PCT/KR2018/012025
§ 371 (c)(1),
(2) Date: Jun. 11, 2020

(87) PCT Pub. No.: WO2019/168249
PCT Pub. Date: Sep. 6, 2019

(65) Prior Publication Data
US 2021/0170381 A1 Jun. 10, 2021

(30) Foreign Application Priority Data

Feb. 27, 2018 (KR) .................. 10-2018-0023819
Oct. 8, 2018 (KR) .................. 10-2018-0119906

(51) Int. Cl.
*B01J 31/24* (2006.01)
*B01J 31/12* (2006.01)
*C07C 2/32* (2006.01)
*C07F 9/50* (2006.01)
*C07C 11/04* (2006.01)

(52) U.S. Cl.
CPC .............. *B01J 31/24* (2013.01); *B01J 31/12* (2013.01); *C07C 2/32* (2013.01); *C07F 9/50* (2013.01); *C07C 11/04* (2013.01)

(58) Field of Classification Search
CPC ........ B01J 31/24; B01J 31/12; B01J 31/2409; B01J 2231/20; B01J 2531/62; B01J 2540/22; B01J 31/14; B01J 31/143; B01J 31/2404; B01J 2531/64; C07C 2/32; C07C 11/04; C07C 2/36; C07C 2531/14; C07C 2531/24; C07C 11/02; C07F 9/50; C07F 9/5027; C07F 11/005; C07F 9/5022; C07F 9/5045; Y02P 20/52
See application file for complete search history.

(56) References Cited

U.S. PATENT DOCUMENTS

| | | | |
|---|---|---|---|
| 6,800,702 B2 | 10/2004 | Wass | |
| 7,511,183 B2 | 3/2009 | Blann et al. | |
| 9,375,709 B2 | 6/2016 | Han et al. | |
| 9,487,456 B2 | 11/2016 | Overett et al. | |
| 9,533,923 B2 | 1/2017 | Mogorosi et al. | |
| 2007/0185360 A1 | 8/2007 | Buchanan et al. | |
| 2015/0045603 A1* | 2/2015 | Han | B01J 31/143 |
| | | | 585/511 |
| 2019/0308178 A1* | 10/2019 | Lee | B01J 31/223 |

FOREIGN PATENT DOCUMENTS

| | | |
|---|---|---|
| CN | 1566041 A | 1/2005 |
| KR | 1020060002741 A | 1/2006 |
| KR | 1020130105126 A | 9/2013 |
| KR | 1020150016959 A | 2/2015 |
| KR | 1020160006192 A | 1/2016 |
| WO | 0204119 A1 | 1/2002 |
| WO | 2004056479 A1 | 7/2004 |

OTHER PUBLICATIONS

Carter et al., "High activity ethylene trimerisation catalysts based on diphosphine ligands", Chemical Communications, 2002, pp. 858-859, vol. 8.
Kulangara et al., "Synthesis and Catalytic Oligomerization Activity of Chromium Catalysts of Ligand Systems with Switchable Connectivity", Organomettalics, 2012, pp. 6438-6449, vol. 31, No. 17.
Oliana et al., "Practical Synthesis of Chiral Vinylphosphine Oxides by Direct Nucleophilic Substitution. Stereodivergent Synthesis of Aminophosphine Ligands", Journal of Organic Chemistry, 2006, pp. 2472-2479, vol. 71, No. 6.
Overett et al., "Carbon-bridged diphosphine ligands for chromium-catalysed ethylene tetramerisation and trimerisation reactions", Journal of Molecular Catalysis A: Chemical, 2008, pp. 114-119, vol. 283, Issues 1-2.

(Continued)

*Primary Examiner* — Ali Z Fadhel
(74) *Attorney, Agent, or Firm* — The Webb Law Firm

(57) ABSTRACT

The present invention relates to a ligand, an ethylene oligomerization catalyst including the ligand, and a method for selectively producing 1-hexene or 1-octene from ethylene by using the catalyst. The ligand according to the present invention is a bis(diphenylphosphino)ethene with a phosphorus atom substituted with a fluoro-substituted phenyl, and when the ligand is used for ethylene oligomerization, the high temperature activity of the catalyst can be increased.

16 Claims, No Drawings

(56) References Cited

OTHER PUBLICATIONS

Yang et al., "Selective Ethylene Oligomerization with Chromium Complexes Bearing Pyridine-Phosphine Ligands: Influence of Ligand Structure on Catalytic Behavior", Organomettalics, 2014, pp. 5749-5757, vol. 33, No. 20.

Zhang et al., "Switchable Ethylene Tri-/Tetramerization with High Activity: Subtle Effect Presented by Backbone-Substituent of Carbon-Bridged Diphosphine Ligands", ACS Catalysis, 2013, pp. 2311-2317, vol. 3, No. 10.

\* cited by examiner

LIGAND, OLIGOMERIZATION CATALYST COMPRISING SAME, AND METHOD FOR PRODUCING ETHYLENE OLIGOMER BY USING OLIGOMERIZATION CATALYST

CROSS-REFERENCE TO RELATED APPLICATIONS

This application is the United States national phase of International Application No. PCT/KR2018/012025 filed Oct. 12, 2018, and claims priority to Korean Patent Application Nos. 10-2018-0023819 and 10-2018-0119906 filed Feb. 27, 2018 and Oct. 8, 2018, respectively, the disclosures of which are hereby incorporated by reference in their entirety.

TECHNICAL FIELD

The present invention relates to a ligand for preparing a highly active and highly selective ethylene oligomerization catalyst to be used in an oligomerization reaction such as trimerization or tetramerization of ethylene, an oligomerization catalyst comprising the ligand, and a method for producing 1-hexene or 1-octene by using the oligomerization catalyst.

BACKGROUND ART

An oligomer, specifically, 1-hexene or 1-octene, is an important commercial raw material widely used in a polymerization process as a monomer or a comonomer for producing linear low density polyethylene, and is obtained by purifying a product produced by an oligomerization reaction of ethylene. However, a conventional oligomerization reaction of ethylene has an ineffective aspect in that significant amounts of butene, higher oligomers, and polyethylene are produced together with 1-hexene or 1-octene. In the case of the technique of such a conventional oligomerization of ethylene, in general, various α-olefins are produced according to the Schulze-Flory or Poisson product distribution, and thus a yield of a desired product is limited.

Recently, studies have been conducted on production of 1-hexene by selective trimerization of ethylene or on production of 1-octene by selective tetramerization of ethylene through transition metal catalysis, and most of the known transition metal catalysts are chromium-based catalysts.

International Patent Publication No. WO 02/04119 discloses a chromium-based catalyst by using a ligand of General Formula $(R^1)(R^2)X$—Y—$X(R^3)(R^4)$ as an ethylene trimerization catalyst, wherein X is phosphorus, arsenic, or antimony, Y is a linking group such as —$N(R^5)$—, and at least one of $R^1$, $R^2$, $R^3$, and $R^4$ has a polar or electron donating substituent.

Another known document discloses a PNP ligand in which methoxy which is a polar substituent is attached at the ortho position of a phenyl ring bonded to phosphorus such as (o-methoxyphenyl)$_2$PN(Me)P(o-methoxyphenyl)$_2$, as a ligand that exhibits catalytic activity with respect to 1-hexene under catalytic conditions (Antea Carter et al., Chem. Commun., 2002, p. 858-859).

In addition, it is known from Korean Patent Laid-Open Publication No. 2006-0002741 that it is practically possible to implement excellent ethylene trimerization activity and selectivity by using a PNP ligand containing a non-polar substituent at the ortho position of a phenyl ring bonded to phosphorus such as (o-ethylphenyl)$_2$PN(Me)P(o-ethylphenyl)$_2$.

Meanwhile, it is known from International Patent Publication No. WO 04/056479 that selectivity in a production of 1-octene is improved by tetramerizing ethylene by using a chromium-based catalyst containing a PNP ligand having no substituent on a phenyl ring bonded to phosphorus. In International Patent Publication No. WO 04/056479, as an example of a heteroatom ligand used in a tetramerization catalyst for ethylene tetramerization, (phenyl)$_2$PN(isopropyl)P(phenyl)$_2$ or the like is disclosed.

The above related art discloses that the chromium-based catalyst containing a heteroatom ligand having nitrogen and phosphorus as heteroatoms may be used to tetramerize ethylene even without a polar substituent with respect to hydrocarbyl or a heterohydrocarbyl group bonded to the phosphorus atom, such that 1-octene may be produced with selectivity over 70 mass %.

However, the related arts do not suggest a concrete example of a ligand structure including a heteroatom, which may tetramerize ethylene to produce 1-octene or trimerize ethylene to produce 1-hexene with high selectivity, merely suggest a PNP-type skeleton structure such as $(R^1)(R^2)P$—$(R^5)N$—$P(R^3)(R^4)$ as a ligand having about 70 mass % of 1-octene selectivity, and limitedly disclose types of substituents that are substitutable in the heteroatom ligand.

Meanwhile, in a case where a catalyst system for tetramerizing ethylene is used, catalytic activity is reduced at high reaction temperature, and significant amounts of polymers (by-products) are produced, which leads to reduction of the selectivity. Therefore, a serious problem occurs in a polymerization process.

Specifically, in a case where a tetramerization catalyst system is used, catalytic activity is reduced at a high temperature, which leads to reduction of a production amount and selectivity of olefin, in particular, 1-octene. In addition, plugging and fouling occur due to an increase in production of by-products, which unavoidably causes shutting down. As a result, a serious problem occurs in an olefin polymerization process.

Therefore, it is urgent to develop an oligomerization catalyst having a structure capable of implementing highly active and highly selective oligomerization of ethylene to produce 1-hexene or 1-octene while not reducing catalytic activity of olefin oligomerization.

DISCLOSURE

Technical Problem

An object of the present invention is to provide a new ligand capable of implementing highly active and highly selective production of an oligomer by maintaining activity even at a high temperature during an oligomerization reaction such as trimerization or tetramerization of ethylene, an oligomerization catalyst comprising the ligand, and a method for producing an ethylene oligomer by using the oligomerization catalyst.

Technical Solution

In one general aspect, there is provided a new ligand capable of implementing highly active and highly selective oligomerization of ethylene even at a high temperature to be used in oligomerization of olefin, specifically, in a trimerization or tetramerization reaction of ethylene, wherein the ligand is represented by the following Formula 1.

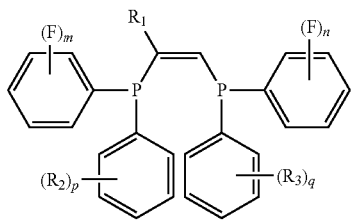

[Formula 1]

In Formula 1,
R₁ is hydrocarbyl;
R₂ and R₃ are each independently hydrocarbyl;
p and q are each independently an integer of 0 to 5; and
m and n are each independently an integer of 0 to 5, where 1≤m+n≤10.

In an exemplary embodiment of the present invention, the ligand may be represented by the following Formula 2.

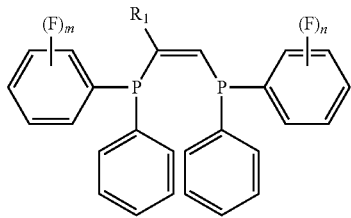

[Formula 2]

In Formula 2, R₁, m, and n are defined as in Formula 1.

In an exemplary embodiment of the present invention, the ligand may be represented by the following Formula 3, 4, or 5.

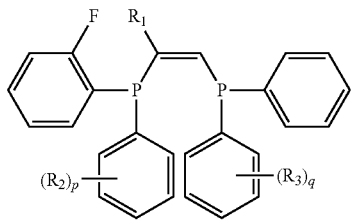

[Formula 3]

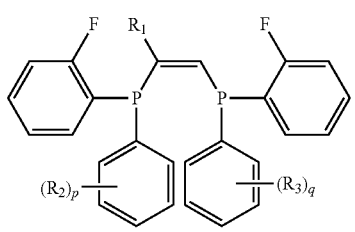

[Formula 4]

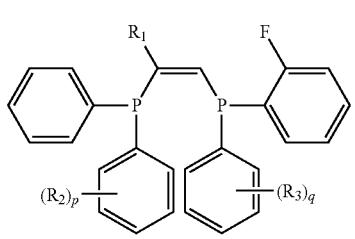

[Formula 5]

In Formulas 3 to 5, $R_1$, $R_2$, $R_3$, p, and q are defined as in Formula 1.

More preferably, in Formulas 3 to 5, $R_1$ may be C1-C7alkyl or C6-C12aryl.

In another general aspect, an ethylene oligomerization catalyst comprises: the ligand of Formula 1; and a transition metal.

In the oligomerization catalyst according to an exemplary embodiment of the present invention, the oligomerization catalyst may be mononuclear or binuclear.

In the oligomerization catalyst according to an exemplary embodiment of the present invention, the transition metal may be, but is not particularly limited to, a Group 4, Group 5, or Group 6 transition metal.

In the oligomerization catalyst according to an exemplary embodiment of the present invention, the transition metal may be chromium, molybdenum, tungsten, titanium, tantalum, vanadium, or zirconium.

In the oligomerization catalyst according to an exemplary embodiment of the present invention, the transition metal may be chromium.

In still another general aspect, there is provided a method for producing an ethylene oligomer by using a catalyst composition including the ethylene oligomerization catalyst, wherein the ethylene oligomer may be produced by contacting the ethylene oligomerization catalyst composition with ethylene.

In the method for producing an ethylene oligomer according to an exemplary embodiment of the present invention, the catalyst composition may further include a cocatalyst.

In the method for producing an ethylene oligomer according to an exemplary embodiment of the present invention, the cocatalyst may be an organoaluminum compound, an organoboron compound, an organic salt, or a mixture thereof, but is not limited thereto.

In the method for producing an ethylene oligomer according to an exemplary embodiment of the present invention, the organoaluminum compound may include an organoaluminoxane-based compound, a compound of $AlR_3$ (wherein R is each independently C1-C12alkyl, C6-C20aryl, C2-C10alkenyl, C2-C10alkynyl, C1-C12alkoxy, or halogen), or $LiAlH_4$, and specifically, the cocatalyst may be methylaluminoxane (MAO), modified methylaluminoxane (mMAO), ethyl aluminoxane (EAO), tetraisobutyl aluminoxane (TIBAO), isobutyl aluminoxane (IBAO), trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, or methylaluminum sesquichloride, but is not limited thereto.

In the method for producing an ethylene oligomer according to an exemplary embodiment of the present invention, the ethylene oligomer may be 1-hexene, 1-octene, or a mixture thereof.

In the method for producing an ethylene oligomer according to an exemplary embodiment of the present invention, an aliphatic hydrocarbon may be used as a reaction solvent.

In the method for producing an ethylene oligomer according to an exemplary embodiment of the present invention, the aliphatic hydrocarbon may be at least one selected from hexane, heptane, octane, nonane, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but is not limited thereto.

Advantageous Effects

The oligomerization catalyst according to the present invention comprises a ligand of Formula 1 which is bis(diphenylphosphino)ethene having an asymmetric structure in which phenyl bonded to a phosphorus atom is substituted with at least one fluorine, and one carbon atom is substituted with substituted or unsubstituted hydrocarbyl other than hydrogen, such that when the oligomerization catalyst according to the present invention is used, catalytic activity and selectivity are excellent even at a high temperature during the oligomerization of ethylene.

In particular, in a case where fluorine is attached to the ortho position of phenyl in the ligand of Formula 1, catalytic activity and selectivity are excellent at a high temperature during oligomerization of ethylene.

Further, when the oligomerization catalyst of the present invention is used, catalytic activity is excellent even at a high temperature, and fouling and plugging caused by a polymer which is a by-product when an oligomer is mass-produced do not occur, such that shutting down is not required, which is very cost-efficient.

Further, when the method for producing an oligomer of the present invention is used, the oligomer may be produced with high activity and high selectivity even at a high temperature, and fouling and plugging do not occur, such that olefin may be produced through a very efficient process.

Best Mode

The term "hydrocarbyl" or "heterohydrocarbyl" used herein refers to a radical having one bonding position derived from a hydrocarbon or a heterohydrocarbon, and the term "hetero" means that a carbon is replaced with one or more atoms selected from O, S, and N atoms.

The term "substituted" used herein refers to a group or moiety having one or more substituents attached to a structural skeleton of the group or the moiety. The term "substituted" means that, at a group or a structural skeleton which is mentioned without limitation, substitution is performed with one or more selected from deuterium, hydroxy, halogen, carboxyl, cyano, nitro, oxo (=O), thioxo (=S), alkyl, haloalkoxy, alkenyl, alkynyl, aryl, aryloxy, alkoxycarbonyl, alkylcarbonyloxy, alkenylcarbonyloxy, alkynylcarbonyloxy, aminocarbonyl, alkylcarbonylamino, alkenylcarbonylamino, alkynylcarbonylamino, thioalkyl, thioalkenyl, thioalkynyl, alkylsilyl, alkenylsilyl, alkynylsilyl, arylsilyl, arylalkyl, arylalkenyl, arylalkynyl, cycloalkyl, cycloalkylalkyl, cycloalkenyl, amino, alkylamino, dialkylamino, heteroaryl, a heterocyclic alkyl ring, heteroarylalkyl, and heterocycloalkyl.

Specifically, the term "substituted" means that substitution is performed with one or more selected from deuterium, hydroxy, halogen, carboxyl, cyano, nitro, oxo (=O), thioxo (=S), C1-C10alkyl, haloC1-C10alkoxy, C2-C10alkenyl, C2-C10alkynyl, C6-C20aryl, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C6-C20arylC1-C10alkyl, C6-C20arylC2-C10alkenyl, C6-C20arylC2-C10alkynyl, C3-C10cycloalkyl, C3-C10cycloalkylC1-C10alkyl, C2-C10cycloalkenyl, amino, C1-C10alkylamino, diC1-C10alkylamino, C6-C20heteroaryl, a C3-C20heterocyclic alkyl ring, C3-C10heteroarylC1-C10alkyl, and C3-C10heterocycloalkyl.

The term "alkyl" used herein refers to a monovalent linear or branched saturated hydrocarbon radical composed of only a carbon atom and a hydrogen atom. Examples of the alkyl include, but are not limited to, methyl, ethyl, propyl, isopropyl, butyl, isobutyl, t-butyl, pentyl, hexyl, octyl, nonyl and the like. In addition, the alkyl radical used in the present invention has 1 to 10 carbon atoms, preferably 1 to 7 of carbon atoms, and more preferably 1 to 5 of carbon atoms.

In addition, the term "aryl" used herein is a monovalent organic radical derived from an aromatic hydrocarbon by removing one hydrogen atom, includes a single or fused ring system that contains preferably 4 to 7 ring atoms and preferably 5 or 6 ring atoms in each ring, and even includes a plurality of aryls linked by a single bond. Specific examples of aryl include phenyl, naphthyl, biphenyl, anthryl, indenyl, fluorenyl and the like, but are not limited thereto. In addition, an aryl radical used herein has 6 to 20 carbon atoms, and preferably 6 to 12 carbon atoms.

The term "ethylene oligomerization" used herein means that ethylene is oligomerized, and is referred to as trimerization or tetramerization depending on the number of ethylenes to be polymerized. In particular, herein, the term "ethylene oligomerization" means that 1-hexene, 1-octene, or a mixture thereof, which is a main comonomer of linear low density polyethylene (LLDPE), is produced from ethylene.

Herein, the term "oligomerization catalyst" refers to an oligomerization catalyst comprising both a transition metal complex consisting of a ligand and a transition metal and a composition including a ligand and a transition metal.

Herein, the term "oligomerization catalyst composition" refers to the "oligomerization catalyst" further including a cocatalyst or an additive.

The present invention provides a ligand for preparing an oligomerization catalyst maintaining high activity even at a high temperature unlike a conventional catalyst. The ligand of the present invention is represented by the following Formula 1.

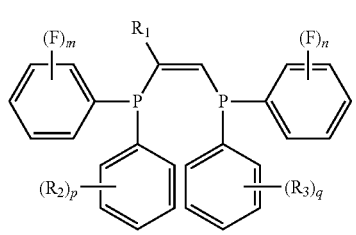

[Formula 1]

In Formula 1,
$R_1$ is substituted or unsubstituted hydrocarbyl;
$R_2$ and $R_3$ are each independently hydrocarbyl;
p and q are each independently an integer of 0 to 5; and
m and n are each independently an integer of 0 to 5, where $1 \le m+n \le 10$.

The ligand of the present invention is a ligand of Formula 1 which is bis(diphenylphosphino)ethene having an asymmetric structure in which phenyl bonded to a phosphorus atom is substituted with at least one fluorine, and one carbon atom is substituted with substituted or unsubstituted hydrocarbyl other than hydrogen, unlike the ligand in the related arts. Catalytic activity and selectivity are excellent even at a high temperature during oligomerization of ethylene due to the ligand of Formula 1 having phenyl substituted with at least one fluorine.

In an exemplary embodiment of the present invention, the ligand may preferably be represented by the following Formula 2.

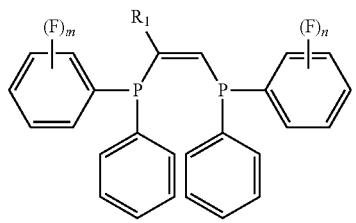

[Formula 2]

In Formula 2, $R_1$, m, and n are defined as in Formula 1.

In an exemplary embodiment of the present invention, the ligand may preferably be represented by the following Formula 3, 4, or 5.

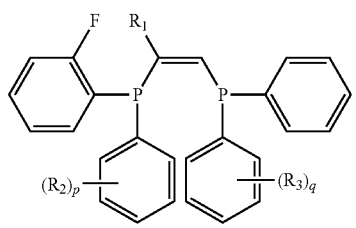

[Formula 3]

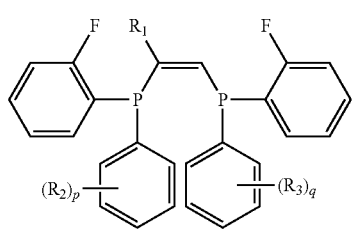

[Formula 4]

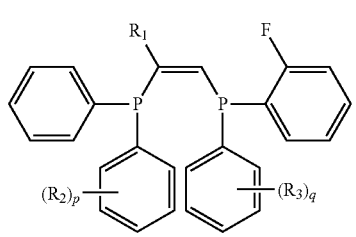

[Formula 5]

In Formulas 3 to 5, $R_1$, $R_2$, $R_3$, p, and q are defined as in Formula 1.

More preferably, in an exemplary embodiment of the present invention, in Formula 1 or 2, m and n are each independently 0 or 1, and m+n may be 1 or 2 ($1 \leq m+n \leq 2$), and fluorine may be substituted at the ortho position.

Specifically, in Formula 1 or 2, m may be 0 and n may be 1.

Specifically, in Formula 1 or 2, m may be 1 and n may be 0.

Specifically, in Formula 1 or 2, m may be 1 and n may be 1.

In an exemplary embodiment of the present invention, $R_2$ and $R_3$ may be each independently C1-C10alkyl, C6-C20aryl, C6-C20arylC1-C10alkyl, or C1-C10alkylC6-C20aryl, and p and q may be each independently an integer of 0 to 2.

More preferably, in an exemplary embodiment of the present invention, p and q may be each independently an integer of 0.

In an exemplary embodiment of the present invention, $R_1$ may be preferably C1-C10alkyl, C6-C20aryl, C6-C20arylC1-C10alkyl, or C1-C10alkylC6-C20aryl, and $R_1$ may more be preferably C1-C7alkyl or C6-C12aryl.

The ligand according to an exemplary embodiment of the present invention may be exemplified by the following structures, but is not limited thereto.

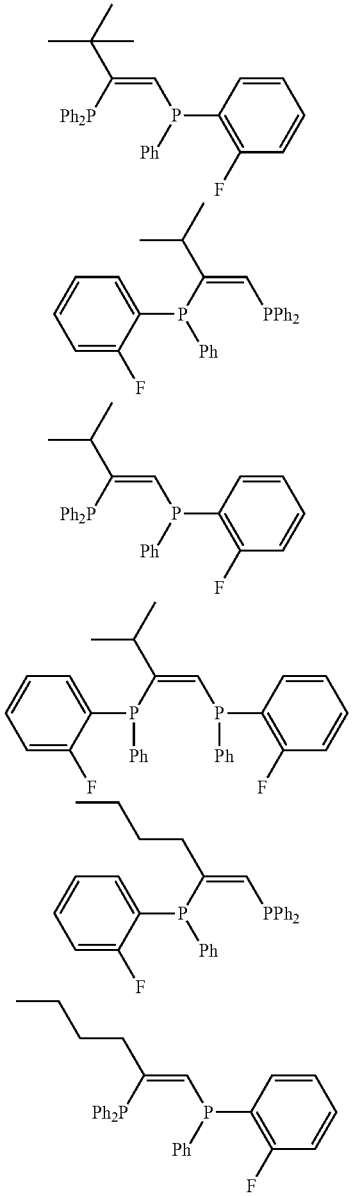

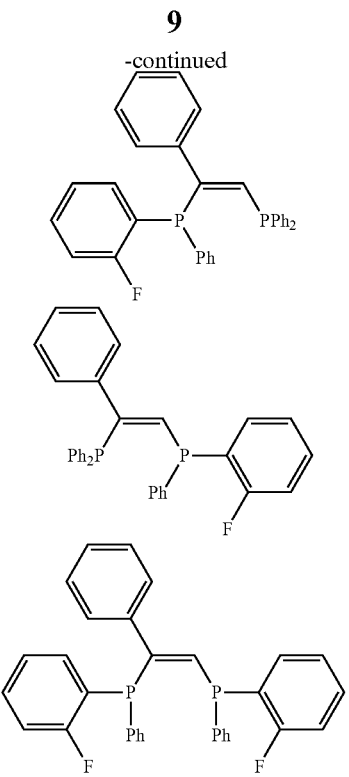

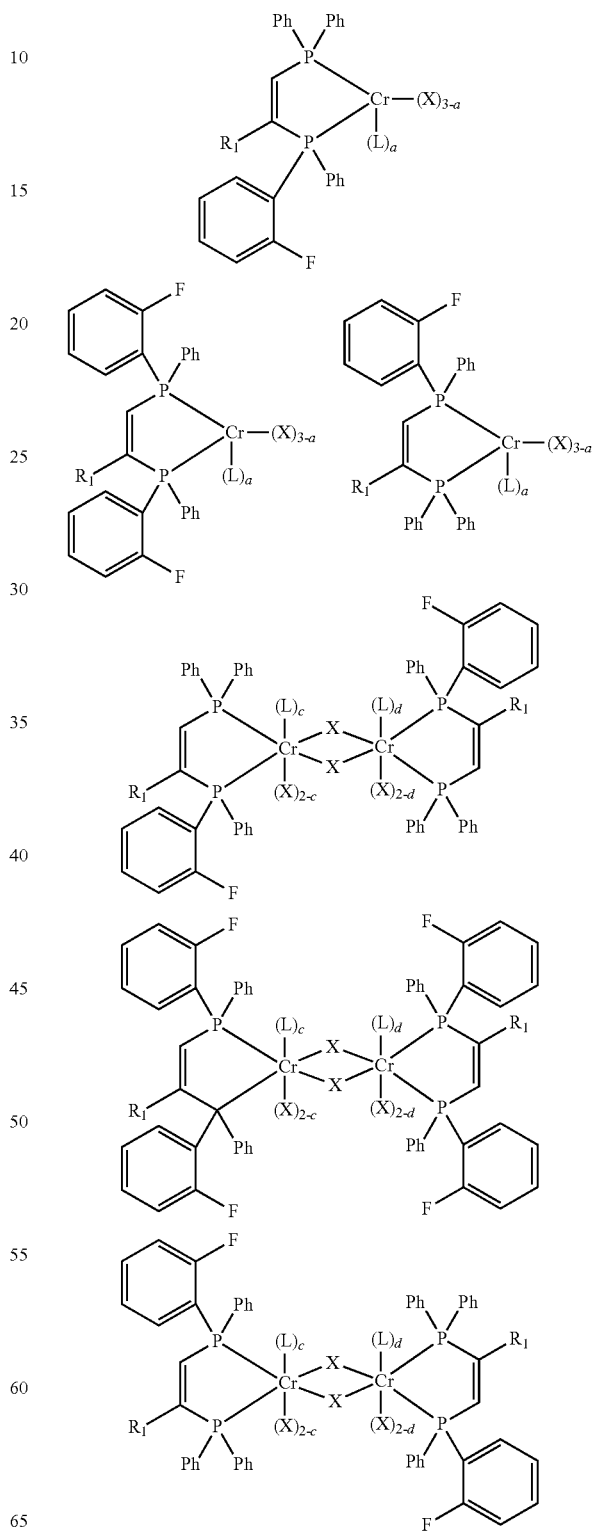

In addition, the present invention provides an ethylene oligomerization catalyst comprising: the ligand of Formula 1; and a transition metal.

The transition metal is not particularly limited, but may be a Group 4, Group 5, or Group 6 transition metal, and may be preferably selected from chromium, molybdenum, tungsten, titanium, tantalum, vanadium, or zirconium. The transition metal is more preferably chrome.

The transition metal may be derived from a transition metal precursor.

Specifically, the transition metal precursor is a Group 4, Group 5, or Group 6 transition metal precursor, and may be preferably selected from a chromium, molybdenum, tungsten, titanium, tantalum, vanadium, or zirconium precursor. A chromium precursor may be more preferably used.

The chromium precursor is not particularly limited, but may be selected from the group consisting of chromium (III) acetylacetonate, chromium (III) chloride tris-tetrahydrofuran, and chromium (III) 2-ethylhexanoate.

The oligomerization catalyst according to the present invention may be a mononuclear or binuclear oligomerization catalyst in which a heteroatom ligand of Formula 1 is coordinated to a transition metal or a transition metal precursor, and specifically may be represented by $ML^1(L)_a(X)_b$ or $M_2X^1{}_2L^1{}_2(L)_y(X)_z$, wherein M may be a transition metal, $L^1$ may be a ligand of Formula 1, X and $X^1$ may be each independently a functional group derived from a transition metal precursor, for example, halogen, L may be an organic ligand, a may be an integer of 0 or more, b may be an integer of (oxidation number of M-a), y may be an integer of 0 or more, and z may be an integer of (2× oxidation number of M)-2-y.

The oligomerization catalyst according to the present invention may allow the ligand having p and q of 0 in Formula 3, 4, or 5 to coordinate to chromium or a chromium precursor, such that it is possible to produce 1-hexene or 1-octene with high activity and high selectivity while stably maintaining oligomerization reaction activity.

Specifically, the oligomerization catalyst according to the present invention may be exemplified by the following structures, but the present invention is not limited thereto.

(In the above structures, $R_1$ is C1-C7alkyl or C6-C12aryl, X is halogen, L is an organic ligand, a is an integer of 0 to 3, and c and d are each independently an integer of 0 to 2.)

Specifically, the organic ligand L according to an exemplary embodiment of the present invention may be selected from the following structures, but the present invention is not limited thereto.

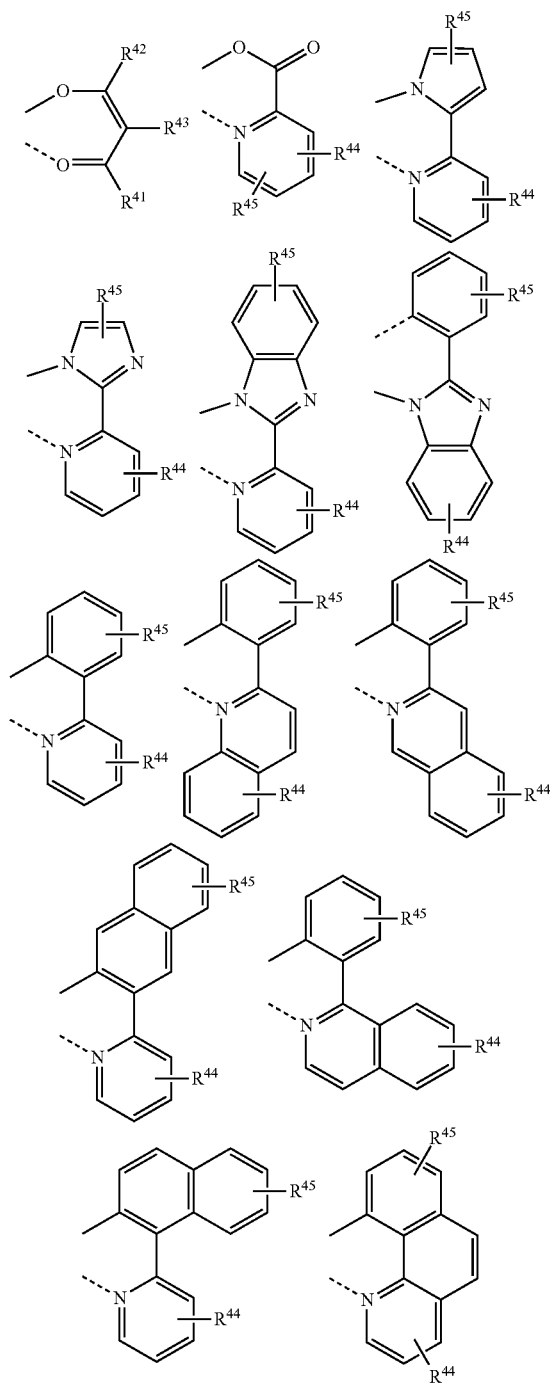

In the above structures, $R^{41}$ and $R^{42}$ are each independently hydrocarbyl, substituted hydrocarbyl, heterohydrocarbyl, or substituted heterohydrocarbyl, and $R^{43}$ is hydrogen, halogen, hydrocarbyl, substituted hydrocarbyl, heterohydrocarbyl, or substituted heterohydrocarbyl; and $R^{44}$ and $R^{45}$ are each independently hydrogen, hydrocarbyl, substituted hydrocarbyl, heterohydrocarbyl, or substituted heterohydrocarbyl.

The ligand constituting the oligomerization catalyst according to the present invention may be prepared using various methods known to those skilled in the art.

When the oligomerization catalyst according to the present invention is used, catalytic activity is excellent, selectivity is very high, and the amount of catalyst to be added may be controlled during oligomerization of olefin. Furthermore, an excellent activity is maintained even at a high temperature, and thus fouling and plugging do not occur in a production process of olefin, which is very cost-efficient and effective.

In addition, the present invention provides a method for producing 1-hexene or 1-octene from ethylene with high activity and high selectivity by using a catalyst composition including the oligomerization catalyst. An ethylene oligomer may be produced by contacting the ethylene oligomerization catalyst composition with ethylene.

The ethylene oligomerization catalyst composition according to an exemplary embodiment of the present invention may further include a cocatalyst for more effective activity and high selectivity.

The ethylene oligomerization catalyst composition may be an oligomerization catalyst system including an oligomerization catalyst comprising a transition metal or a transition metal precursor, and a ligand of Formula 1, and a cocatalyst.

The cocatalyst may be in principle any compound that activates a transition metal complex in which a ligand of Formula 1 is coordinated. The cocatalyst may also be a mixture. Examples of a compound suitable as the cocatalyst include an organoaluminum compound, organoaluminoxane, an organoboron compound, and an organic salt.

Examples of the organoaluminum compound suitable for being used as an activator in the ethylene oligomerization catalyst composition according to an exemplary embodiment of the present invention may include a compound of $AlR_3$ (wherein R is each independently C1-C12alkyl, C6-C20aryl, C2-C10alkenyl, C2-C10alkynyl, C1-C12alkoxy, or halogen) or $LiAlH_4$.

The organoaluminum compound may include one or a mixture of two or more of trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, methylaluminum sesquichloride, and aluminoxane.

Organoaluminoxane suitable for being used as an activator in the ethylene oligomerization catalyst composition according to an exemplary embodiment of the present invention is an oligomer compound capable of being prepared by adding water to an alkylaluminum compound such as trimethylaluminum. The resulting aluminoxane oligomer compound may be a linear, cyclic, or cage compound, or a mixture thereof.

The organoaluminoxane may be selected from alkylaluminoxane such as methylaluminoxane (MAO), ethyl aluminoxane (EAO), tetraisobutyl aluminoxane (TIBAO), and isobutyl aluminoxane (IBAO), and modified alkylaluminoxane such as modified methylaluminoxane (MAO). Modified methylaluminoxane (manufactured by Akzo Nobel N.V.) contains a mixed alkyl group such as an isobutyl or n-octyl group, in addition to a methyl group. As a specific example, the organoaluminoxane may be one or a mixture of two or more selected from methylaluminoxane (MAO), modified methylaluminoxane (MAO), ethyl aluminoxane (EAO), tetraisobutyl aluminoxane (TIBAO), and isobutyl aluminoxane (IBAO).

The organoboron compound suitable for being used as an activator in the ethylene oligomerization catalyst composition according to an exemplary embodiment of the present invention may be boroxine, $NaBH_4$, triethylborane, triphenylborane, a triphenylborane ammonia complex, tributylborate, triisopropylborate, tris(pentafluorophenyl)borane, trityl(tetrapentafluorophenyl)borate, dimethylphenylammonium(tetrapentafluorophenyl)borate, diethylphenylammonium(tetrapentafluorophenyl)borate, methyldiphenylammonium(tetrapentafluorophenyl)borate, ethyldiphenylammonium (tetrapentafluorophenyl)borate, or a mixture thereof, and these organoboron compounds may be used as a mixture with the organoaluminum compound.

The cocatalyst may be preferably one or a mixture of two or more selected from the group consisting of methylaluminoxane (MAO), modified methylaluminoxane (mMAO), ethyl aluminoxane (EAO), tetraisobutyl aluminoxane (TIBAO), isobutyl aluminoxane (IBAO), trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride, and more preferably methylaluminoxane (MAO) or modified methylaluminoxane (mMAO).

In an exemplary embodiment of the present invention, a ratio of the oligomerization catalyst to the cocatalyst is 1:1 to 10,000:1, and more preferably 1:1 to 2,000:1, based on a molar ratio of a metal of the cocatalyst to the transition metal. More preferably, a ratio of the oligomerization catalyst to the aluminoxane cocatalyst is 1:1 to 10,000:1, and more preferably 1:1 to 1,000:1, based on a molar ratio of aluminum to the transition metal.

The ethylene oligomerization catalyst composition may further include other components, if possible, as long as they do not impair the spirit of the present invention, in addition to the oligomerization catalyst and the cocatalyst.

The oligomerization catalyst and the cocatalyst, which are individual components of the oligomerization catalyst composition, may be blended simultaneously or sequentially in any order in the presence of a solvent to provide an active catalyst. The mixing of the respective components of the catalyst composition may be performed at a temperature of −20° C. to 250° C. The presence of olefin during the mixing of the respective components may generally exhibit a protective effect, and a catalyst performance may thus be improved. A temperature range is more preferably 20 to 160° C.

The reaction product disclosed in the present invention, in other words, the ethylene oligomer, in particular, 1-hexene or 1-octene, may be produced by a homogeneous liquid phase reaction in the presence of an inert solvent or a two-phase liquid/liquid reaction, or a bulk phase reaction or a gaseous reaction in which a product olefin acts as a main medium with the oligomerization catalyst or the oligomerization catalyst composition according to the present invention, using conventional apparatuses and contact techniques. However, the homogeneous liquid phase reaction in the presence of an inert solvent is preferable.

The method for producing an oligomer according to an exemplary embodiment of the present invention may be performed in an inert solvent. That is, any inert solvent that does not react with the oligomerization catalyst and the cocatalyst of the present invention may be used, and the inert solvent may be an aliphatic hydrocarbon in terms of improving catalytic activity. In the case of the oligomerization catalyst system according to the present invention, it is easy to control the amount of catalyst during continuous addition of a catalyst solution, and an excellent catalytic activity is exhibited.

The aliphatic hydrocarbon is preferably a saturated aliphatic hydrocarbon, and may include a linear saturated aliphatic hydrocarbon represented by $C_nH_{2n+2}$ (wherein n is an integer of 1 to 15), an alicyclic saturated aliphatic hydrocarbon represented $C_mH_{2m}$ (wherein m is an integer of 3 to 8), and a linear or cyclic saturated aliphatic hydrocarbon in which one or two or more lower alkyl groups having 1 to 3 carbon atoms are substituted. Specifically, the aliphatic hydrocarbon may be at least one selected from hexane, heptane, octane, nonane, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but is not limited thereto. The saturated aliphatic hydrocarbon is more preferably methylcyclohexane, cyclohexane, hexane, or heptane.

The oligomerization reaction according to an exemplary embodiment of the present invention may be performed at a temperature of −20 to 250° C., preferably 20 to 160° C., more preferably 60 to 160° C. A reaction pressure may be performed at an atmospheric pressure to 100 bar, and preferably 10 to 70 bar.

In the method for producing an oligomer according to an exemplary embodiment of the present invention, the oligomer may be 1-hexene, 1-octene, or a mixture thereof.

In the method for producing an oligomer according to an exemplary embodiment of the present invention, 1-octene may be obtained in an amount of 60 wt % or more, preferably 70 wt % or more, and more preferably 80 wt % or more, with respect to a total weight of a C8 product produced from ethylene through the oligomerization reaction. In this case, a yield means a weight percentage (wt %) of 1-octene produced with respect to the total weight of the produced C8 product.

In the method for producing an oligomer according to an exemplary embodiment of the present invention, 1-hexene may be obtained in an amount of 50 wt % or more, preferably 70 wt % or more, and more preferably 90 wt % or more, with respect to a total weight of a C6 product produced from ethylene through the oligomerization reaction. In this case, a yield means a weight percentage (wt %) of 1-hexene produced with respect to the total weight of the produced C6 product.

In the method for producing an oligomer according to an exemplary embodiment of the present invention, 1-butene, 2-hexene, 1-decene, methylcyclopentane, methylenecyclopentane, propylcyclopentane, and a number of higher oligomers and polyethylene each in different amounts may be provided in addition to 1-hexene or 1-octene, depending on an oligomerization catalyst and a reaction condition.

The method for producing an oligomer according to an exemplary embodiment of the present invention may be performed with a plant including any type of reactor. Examples of the reactor include, but are not limited to, a batch reactor, a semi-batch reactor, and a continuous reactor.

The plant may include a reactor, an olefin reactor and an inlet of the oligomerization catalyst composition in the reactor, a line for discharging a oligomerization reaction product from the reactor, and at least one separator for separating the oligomerization reaction product in a combination manner. In this case, the catalyst composition may include the oligomerization catalyst and the cocatalyst disclosed in the present invention, or may include a transition metal or a transition metal precursor, a ligand of Formula 1, and a cocatalyst.

By using the oligomerization catalyst or the oligomerization catalyst composition according to the present invention, the activity of the catalyst is maintained even at a high temperature during ethylene oligomerization, and 1-hexene, 1-octene, or a mixture thereof may thus be produced with high activity and high selectivity.

The following examples are provided to describe effects of the present invention in detail. However, the following examples are intended to illustrate the present invention and are not intended to limit the scope of the present invention.

Preparation of Ligand

[Preparation Example A] Preparation of chloro(2-fluorophenyl)phenylphosphine

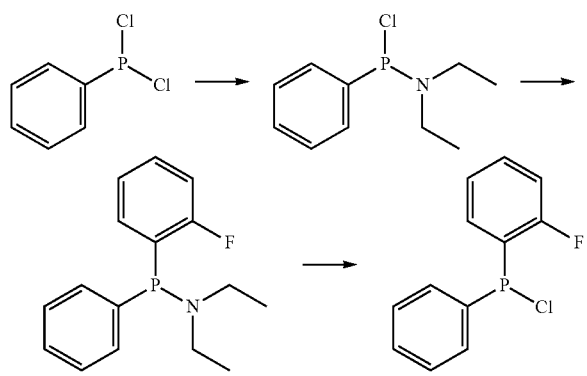

Preparation of N,N-diethylaminochloro(phenyl)phosphine

N,N-Diethylaminochloro(phenyl)phosphine was prepared with reference to the known document (M. Oliana et. al., J. Org. Chem., 2006, p. 2472-2479).

In a dried flask under a nitrogen atmosphere, dichloro (phenyl)phosphine (8.949 g, 50 mmol) was dissolved in n-hexane (400 mL), and then diethylamine (7.314 g, 100 mmol) was slowly added at room temperature. The mixture was reacted for 1 hour or longer, and then was filtered through celite to remove volatile substances under a reduced pressure, thereby obtaining a transparent colorless liquid-type title compound (10.2 g, 94.6%).

$^1$H NMR (500 MHz, $C_6D_6$) δ 7.74 (m, 2H, aromatics), 7.10 (m, 2H, aromatics), 7.03 (m, 1H, aromatics), 2.85 (m, 4H, —$CH_2$—), 0.79 (m, 6H, —$CH_3$).

Preparation of N,N-diethyl-1-(2-fluorophenyl)-1-phenylphosphineamine

In a dried flask under a nitrogen atmosphere, 1-bromo-2-fluorobenzene (7.0 g, 40 mmol) was dissolved in anhydrous THF (30 mL), the temperature was decreased to −78° C., and then 1.6 M n-butyllithium (25.0 mL, 40 mmol, Sigma-Aldrich Corporation) was slowly added. After the mixture was reacted for 1 hour or longer while maintaining a low temperature, the N,N-diethylaminochloro(phenyl)phosphine (8.195 g, 38 mmol) obtained above was slowly added to the mixture, and then a reaction was performed for 2 hours or longer. After a reaction temperature of the mixture was increased to room temperature, and the volatile substances were removed under a reduced pressure, the mixture was diluted with a solution (hexane:dichloromethane (1:1 v/v)) and then was filtered through silica, thereby obtaining a transparent colorless liquid-type title compound (8.967 g, 85.7%).

$^1$H NMR (500 MHz, $C_6D_6$) δ 7.45 (m, 2H, aromatics), 7.34 (m, 1H, aromatics), 7.14 (m, 3H, aromatics), 6.94 (m, 3H, aromatics), 3.00 (m, 4H, —$CH_2$N), 0.83 (t, 6H, —$CH_3$); $^{13}$C NMR (600 MHz, $CDCl_3$) δ 164.3, 138.8, 132.6, 131.2, 130.3, 128.0, 123.9, 115.0, 44.6, 14.4; $^{19}$F NMR (500 MHz, $C_6D_6$) δ −103.7; $^{31}$P NMR (500 MHz, $C_6D_6$) δ 49.7.

Preparation of chloro(2-fluorophenyl)phenylphosphine

In a dried flask under a nitrogen atmosphere, the obtained N,N-diethyl-1-(2-fluorophenyl)-1-phenylphosphineamine (8.967 g, 32.6 mmol) was dissolved in anhydrous diethyl ether (70 mL), and then 1 M hydrogen chloride/diethyl ether (68.4 mL) was slowly added. The mixture was reacted for 1 hour or longer, and then was filtered through active alumina, thereby obtaining a transparent colorless liquid-type title compound (7.377 g, 94.9%).

$^1$H NMR (500 MHz, $C_6D_6$) δ 7.51 (m, 3H, aromatics), 6.97 (m, 3H, aromatics), 6.80 (m, 1H, aromatics), 6.73 (m, 1H, aromatics), 6.58 (m, 1H, aromatics); $^{13}$C NMR (600 MHz, $CDCl_3$) δ 164.4, 137.3, 132.5-128.9, 124.6, 115.4; $^{19}$F NMR (500 MHz, $C_6D_6$) δ −104.8; $^{31}$P NMR (500 MHz, $C_6D_6$) δ 71.4.

[Preparation Example B] Preparation of (2-fluorophenyl)(phenyl)phosphine

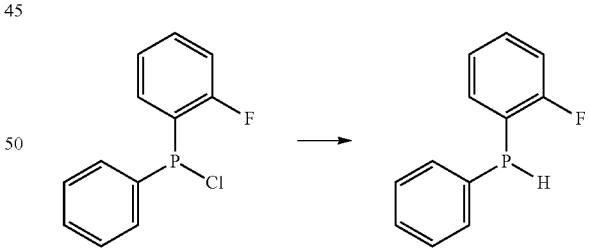

In a dried flask under a nitrogen atmosphere, the chloro (2-fluorophenyl)phenylphosphine (2.3863 g, 10 mmol) obtained in Preparation Example A was dissolved in n-hexane (20 mL), and then trimethyltin hydride (4.0163 g, 11 mmol) was slowly added. The mixture was reacted for 30 minutes, and then filtered through celite to remove volatile substances under a reduced pressure, thereby obtaining a liquid-type title compound (2.0418 g, 100%).

$^1$H NMR (500 MHz, $C_6D_6$) δ 7.37 (m, 2H, aromatics), 7.11 (m, 1H, aromatics), 6.97 (m, 3H, aromatics), 6.80 (m, 1H, aromatics), 6.68 (m, 1H, aromatics), 5.51-5.07 (d, 1H, —P).

[Preparation Example 1] Preparation of Ligand (1)

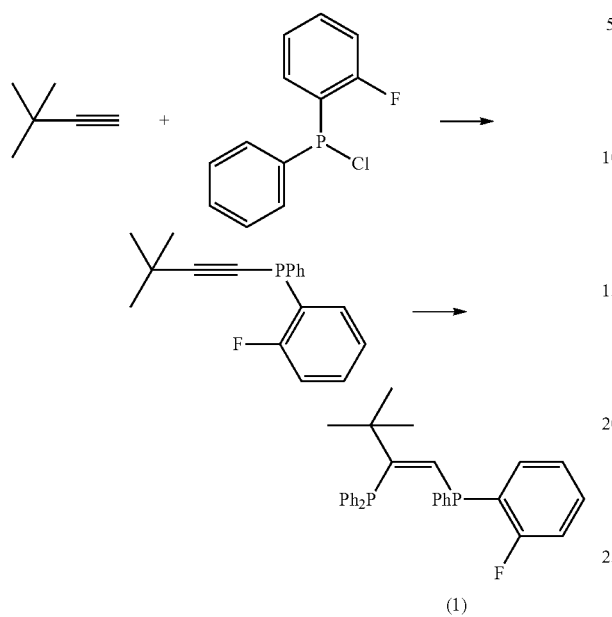

(1)

Preparation of (3,3-dimethyl-1-butynyl)(2-fluoro-phenyl)phenylphosphine

In a dried flask under a nitrogen atmosphere, 3,3-dimethyl-1-butyne (0.2875 g, 3.5 mmol, Sigma-Aldrich Corporation) was dissolved in anhydrous THF (6 mL), the temperature was decreased to −78° C., and then 1.6 M n-butyllithium (1.75 mL, 2.8 mmol, Sigma-Aldrich Corporation) was slowly added. After the mixture was reacted for 1 hour or longer while maintaining a low temperature, the chloro(2-fluorophenyl)phenylphosphine (0.5345 g, 2.24 mmol) obtained in Preparation Example A was slowly added to the mixture, and then a reaction was performed for 2 hours or longer. After a reaction temperature of the mixture was increased to room temperature, and volatile substances were removed under a reduced pressure, the mixture was diluted with a hexane solution and then filtered through celite and dried, thereby obtaining a yellow solid-type title compound (0.6214 g, 97.6%).

$^1$H NMR (500 MHz, CDCl$_3$) δ 7.68 (m, 3H, aromatics), 7.27 (m, 4H, aromatics), 7.13 (m, 1H, aromatics), 6.96 (m, 1H, aromatics); $^{13}$C NMR (600 MHz, CDCl$_3$) δ 165.1, 135.6, 133.1, 132.4, 130.9, 128.4, 124.4, 119.5, 115.2, 72.3, 30.8, 28.8; $^{19}$F NMR (500 MHz, CDCl$_3$) δ −105.5; $^{31}$P NMR (500 MHz, CDCl$_3$) δ −47.0; FT-ICR MS: m/z [M+H]$^+$ calcd for C$_{18}$H$_{19}$FP$^+$: 285.1208; found: 285.1206.

Preparation of Ligand (1)

In a dried flask under a nitrogen atmosphere, the (3,3-dimethyl-1-butynyl)(2-fluorophenyl)phenylphosphine (0.1422 g, 0.5 mmol) prepared above, copper(I) iodide (0.0048 g, 5 mol %), and cesium carbonate (0.0163 g, 10 mol %) were dissolved in dimethylformamide (1 mL), diphenylphosphine (0.1117 g, 0.6 mmol) was slowly added, the temperature was increased to 90° C., and then a reaction was performed for 3 hours. The mixture was purified through a silica column by using a solution (n-hexane:ethyl acetate (9:1 v/v)), thereby obtaining a transparent colorless oil-type ligand (1) (0.2236 g, 95.1%).

$^1$H NMR (500 MHz, CDCl$_3$) δ 7.70 (m, 1H, aromatics), 7.65 (m, 1H, aromatics), 7.46 (m, 4H, aromatics), 7.29 (m, 4H, aromatics), 7.21 (m, 4H, aromatics), 7.21-6.99 (m, 4H, aromatics), 6.85 (m, 1H, aromatics), 1.28 (s, 9H, —CH$_3$); $^{13}$C NMR (600 MHz, CDCl$_3$) δ 165.2, 163.1, 138.9, 135.8, 134.1, 133.0, 128.6, 126.2, 123.8, 119.6, 115.2; $^{31}$P NMR (500 MHz, CDCl$_3$) δ −11.0, −39.0; FT-ICR MS: m/z [M.]$^+$ calcd for C$_{30}$H$_{29}$FP$_2$: 470.1729; found: 470.1718.

[Preparation Example 2] Preparation of Ligand (2)

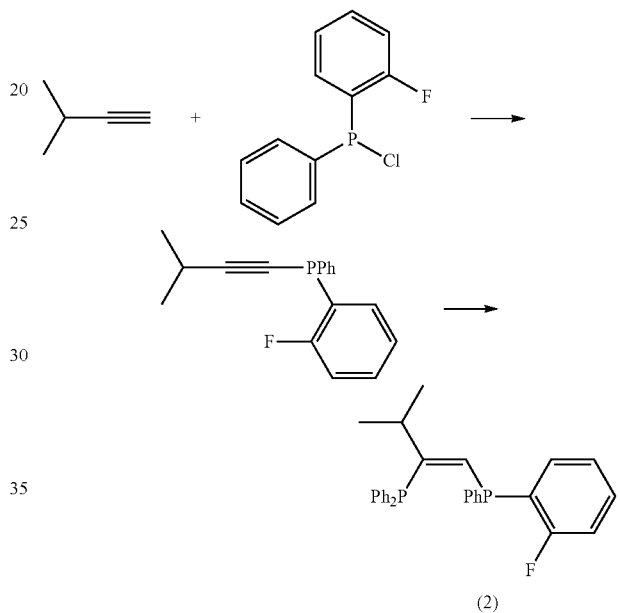

(2)

Preparation of (2-fluorophenyl)(3-methyl-1-butyne)(phenyl)phosphine

A reaction was performed in the same manner as that of the preparation method of Ligand (1) except that 3-methyl-1-butyne was used as a starting material instead of 3,3-dimethyl-1-butyne, thereby obtaining a title compound (80.93%).

$^1$H NMR (500 MHz, CDCl$_3$) δ 7.62 (m, 3H, aromatics), 7.28 (m, 4H, aromatics), 7.09 (m, 1H, aromatics), 6.93 (m, 1H, aromatics), 2.77 (q, 1H, —CH—), 1.26 (d, 2H, —CH$_3$); $^{13}$C NMR (600 MHz, CDCl$_3$) δ 165.1, 135.4, 133.2, 131.1, 128.9, 124.3, 116.8, 115.2, 73.2, 22.7, 22.0; $^{19}$F NMR (500 MHz, CDCl$_3$) δ −105.5; $^{31}$P NMR (500 MHz, CDCl$_3$) δ −46.5; FT-ICR MS: m/z [M+H]$^+$ calcd for C$_{17}$H$_{17}$FP$^+$: 271.1052; found: 271.1049.

Preparation of Ligand (2)

A reaction was performed in the same manner as that of the preparation method of Ligand (1) except that the (2-fluorophenyl)(3-methyl-1-butyne)(phenyl)phosphine obtained above was used as a starting material instead of (3,3-dimethyl-1-butynyl)(2-fluorophenyl)phenylphosphine, thereby obtaining Ligand (2) (90.54%).

$^1$H NMR (500 MHz, CDCl$_3$) δ 7.30 (m, 18H, aromatics), 7.05 (m, 1H, aromatics), 6.98 (m, 1H, =CH—), 2.50 (m, 1H, —CH—), 0.88 (t, 6H, —CH$_3$); $^{13}$C NMR (600 MHz, CDCl$_3$) δ 165.3, 162.2, 138.9, 136.3, 134.8, 133.6, 132.2, 130.7, 128.4, 127.8, 126.3, 124.1, 115.6, 33.5, 24.1; $^{19}$F NMR (500 MHz, CDCl$_3$) δ −102.6; $^{31}$P NMR (500 MHz, CDCl$_3$) δ −4.9, −35.3; FT-ICR MS: m/z [M.]$^+$ calcd for C$_{29}$H$_{27}$FP$_2$: 456.1572; found: 456.1567.

[Preparation Example 3] Preparation of Ligand (3)

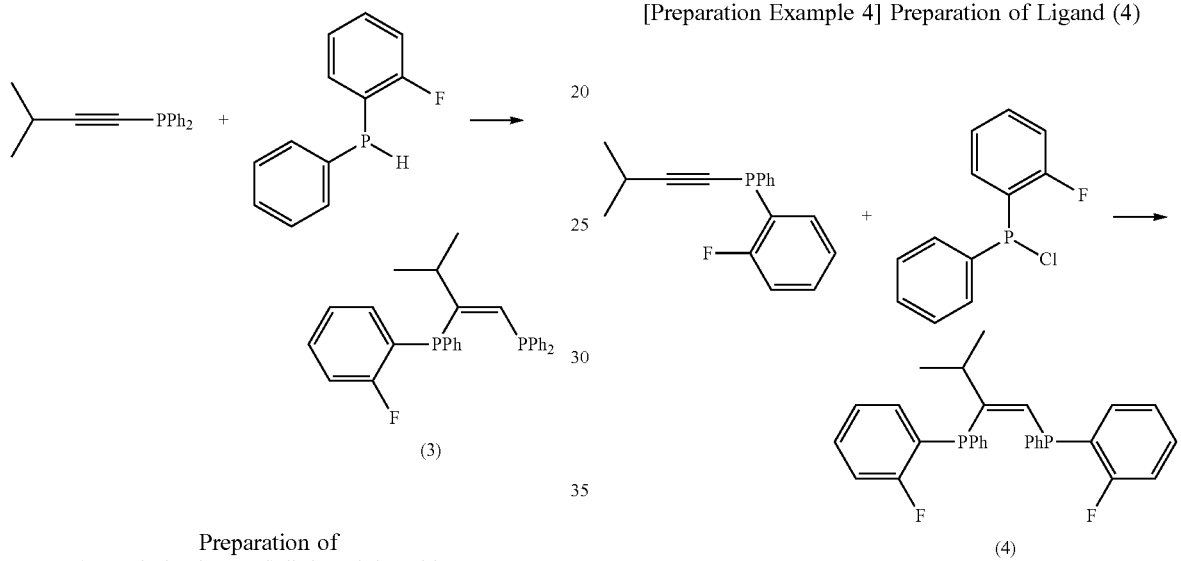

(3)

Preparation of (3-methyl-1-butynyl)diphenylphosphine

In a dried flask under a nitrogen atmosphere, 3-methyl-1-butyne (3.406 g, 50 mmol) was dissolved in anhydrous diethyl ether (40 mL), the temperature was decreased to −78° C., and then 1.6 M n-butyllithium (26.5 mL, 42.5 mmol, Sigma-Aldrich Corporation) was slowly added. After the mixture was reacted for 1 hour or longer while maintaining a low temperature, chlorodiphenylphosphine (8.44 g, 38.2 mmol) was slowly added to the mixture, and then a reaction was performed for 2 hours or longer. After a reaction temperature of the mixture was increased to room temperature, and volatile substances were removed under a reduced pressure, the mixture was diluted with a hexane solution, and then filtered through celite and dried, thereby obtaining a transparent colorless liquid-type title compound (8.9 g, 92.23%).

$^1$H NMR (500 MHz, CDCl$_3$) δ 7.59 (m, 4H, aromatics), 7.30 (m, 6H, aromatics), 2.77 (m, 1H, —CH—), 1.26 (d, 6H, —CH$_3$); $^{13}$C NMR (600 MHz, CDCl$_3$) δ 137.1, 132.3, 128.6, 115.6, 74.7, 22.7, 21.9; $^{31}$P NMR (500 MHz, CDCl$_3$) δ −33.8; FT-ICR MS: m/z [M+H]$^+$ calcd for C$_{17}$H$_{18}$P$^+$: 253.1146; found: 253.1143.

Preparation of Ligand (3)

In a dried flask under a nitrogen atmosphere, the (3-methyl-1-butynyl)diphenylphosphine (0.1261 g, 0.5 mmol) prepared above, copper(I) iodide (0.0048 g, 5 mol %), and cesium carbonate (0.0163 g, 10 mol %) were dissolved in dimethylformamide (1 mL), the (2-fluorophenyl)(phenyl)phosphine (0.1225 g, 0.6 mmol) prepared in Preparation Example B was slowly added, the temperature was increased to 90° C., and then a reaction was performed for 3 hours. The mixture was purified through a silica column by using a solution (n-hexane:ethyl acetate (9:1 v/v)), thereby obtaining a transparent colorless oil-type ligand (3) (0.2282 g, 100.0%).

$^1$H NMR (500 MHz, CDCl$_3$) δ 7.24 (m, 17H, aromatics), 7.05 (m, 2H, aromatics), 6.95 (s, 1H, =CH—), 2.45 (s, 1H, —CH—), 0.99 (t, 3H, —CH$_3$), 0.83 (t, 3H, —CH$_3$); $^{13}$C NMR (600 MHz, CDCl$_3$) δ 165.3, 161.6, 139.5, 134.3, 133.4, 132.8, 130.5, 128.3, 124.0, 115.2, 33.8, 24.1, 23.6; $^{19}$F NMR (500 MHz, CDCl$_3$) δ −101.6; $^{31}$P NMR (500 MHz, CDCl$_3$) δ −16.4, −26.9; FT-ICR MS: m/z [M.]$^+$ calcd for C$_{29}$H$_{27}$FP$_2$: 456.1572; found: 456.1570.

[Preparation Example 4] Preparation of Ligand (4)

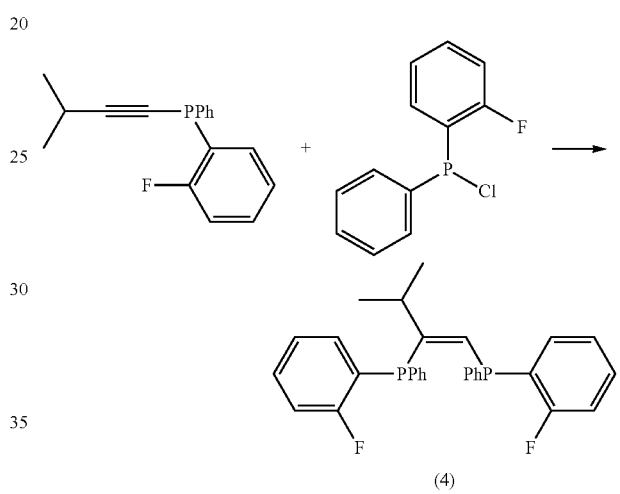

(4)

A reaction was performed in the same manner as that of the preparation method of Ligand (3) except that (2-fluorophenyl)(3-methyl-1-butyne)(phenyl)phosphine was used as a starting material instead of (3-methyl-1-butynyl)diphenylphosphine, thereby obtaining Ligand (4) (63.99%).

$^1$H NMR (500 MHz, CDCl$_3$) δ 7.30-6.99 (m, 15H, aromatics), 7.10 (m, 3H, aromatics), 6.99 (s, 1H, =CH—), 2.47 (s, 1H, —CH—), 1.02 (t, 3H, —CH$_3$), 0.86 (t, 3H, —CH$_3$); $^{13}$C NMR (600 MHz, CDCl$_3$) δ 165.3, 163.4, 161.5, 138.6, 134.8, 133.5, 132.2, 130.8, 128.5, 125.8, 115.3, 33.9, 24.1; $^{19}$F NMR (500 MHz, CDCl$_3$) δ −101.6, −102.6; $^{31}$P NMR (500 MHz, CDCl$_3$) δ −17.0, −36.0; FT-ICR MS: m/z [M.]$^+$ calcd for C$_{29}$H$_{26}$F$_2$P$_2$: 474.1478; found: 474.1471.

[Preparation Example 5] Preparation of Ligand (5)

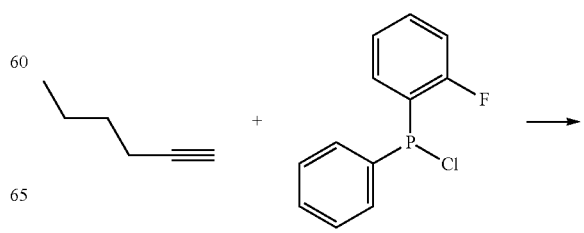

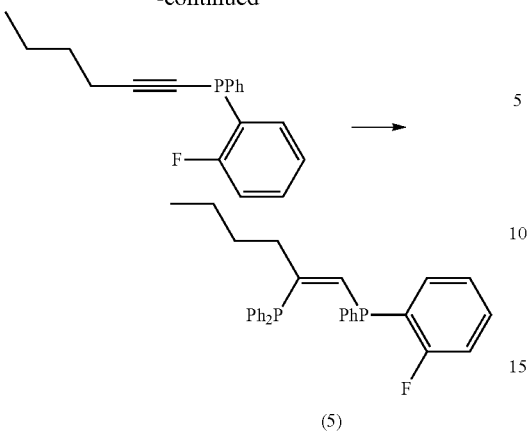

(5)

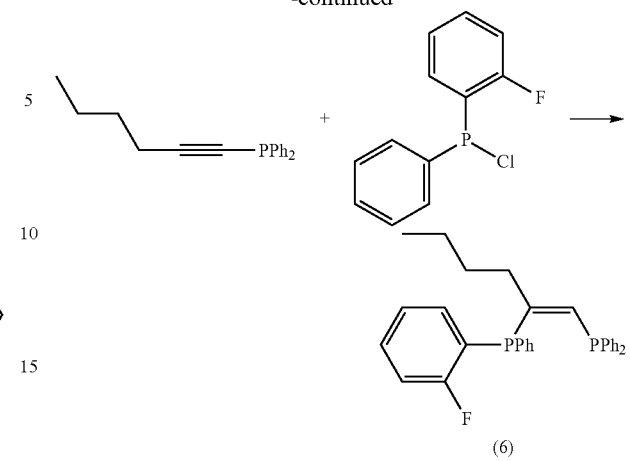

(6)

Preparation of (2-fluorophenyl)(1-hexynyl)(phenyl)phosphine

A reaction was performed in the same manner as that of the preparation method of Ligand (1) except that 1-hexyne was used as a starting material instead of 3,3-dimethyl-1-butyne, thereby obtaining a title compound (79.45%).

$^1$H NMR (500 MHz, CDCl$_3$) δ 7.69-7.62 (m, 3H, aromatics), 7.32 (m, 4H, aromatics), 7.15 (t, 1H, aromatics), 6.97 (m, 1H, aromatics), 2.43 (t, 2H, —CH$_2$—), 1.62 (q, 2H, —CH$_2$—), 1.45 (q, 2H, —CH$_2$—), 0.93 (t, 3H, —CH$_3$); $^{13}$C NMR (600 MHz, CDCl$_3$) δ 165.1, 135.4, 133.3, 132.5, 131.1, 129.0, 124.1, 115.1, 111.6, 74.1, 30.5, 21.9, 20.0, 13.5; $^{19}$F NMR (500 MHz, CDCl$_3$) δ -105.5; $^{31}$P NMR (500 MHz, CDCl$_3$) δ -45.7; FT-ICR MS: m/z [M+H]$^+$ calcd for C$_{19}$H$_{19}$FP$^+$: 285.1208; found: 285.1206.

Preparation of Ligand (5)

A reaction was performed in the same manner as that of the preparation method of Ligand (1) except that (2-fluorophenyl)(1-hexynyl)(phenyl)phosphine was used as a starting material instead of (3,3-dimethyl-1-butynyl)(2-fluorophenyl)phenylphosphine, thereby obtaining Ligand (5) (51.01%).

$^1$H NMR (500 MHz, CDCl$_3$) δ 7.29-7.18 (m, 16H, aromatics), 7.10 (s, 1H, =CH—), 7.02 (m, 1H, aromatics), 6.95 (m, 1H, aromatics), 2.12 (t, 2H, —CH$_2$—), 1.24 (m, 2H, —CH$_2$—), 1.10 (m, 2H, —CH$_2$—), 0.69 (t, 3H, —CH$_3$); $^{13}$C NMR (600 MHz, CDCl$_3$) δ 163.5, 156.5, 138.5, 136.3, 134.6, 133.2, 132.1, 130.6, 128.5, 127.9, 125.9, 115.5, 36.5, 30.9, 22.3, 13.7; $^{19}$F NMR (500 MHz, CDCl$_3$) δ -102.5; $^{31}$P NMR (500 MHz, CDCl$_3$) δ -7.9, -35.1; FT-ICR MS: m/z [M.]$^+$ calcd for C$_{30}$H$_{29}$FP$_2$: 470.1729; found: 470.1729.

[Preparation Example 6] Preparation of Ligand (6)

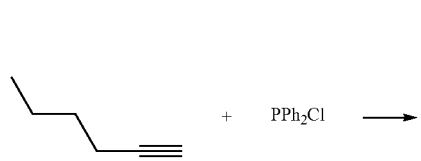

Preparation of 1-hexynyldiphenylphosphine

A reaction was performed in the same manner as that of the preparation method of Ligand (3) except that 1-hexyne was used as a starting material instead of 3-methyl-1-butyne, thereby obtaining a title compound (8.6 g, 84.42%).

$^1$H NMR (500 MHz, CDCl$_3$) δ 7.60 (t, 4H, aromatics), 7.30 (m, 6H, aromatics), 2.44 (t, 2H, —CH$_2$—), 1.60 (q, 2H, —CH$_2$—), 1.46 (m, 2H, —CH$_2$—), 0.90 (t, 3H, —CH$_3$); $^{13}$C NMR (600 MHz, CDCl$_3$) δ 137.0, 132.2, 128.4, 110.4, 75.6, 30.5, 21.9, 20.0, 13.5; $^{31}$P NMR (500 MHz, CDCl$_3$) δ -33.0; FT-ICR MS: m/z [M+H]$^+$ calcd for C$_{18}$H$_{20}$P$^+$: 267.1303; found: 267.1300.

Preparation of Ligand (6)

A reaction was performed in the same manner as that of the preparation method of Ligand (3) except that the 1-hexynyldiphenylphosphine prepared above was used as a starting material instead of (3-methyl-1-butynyl)diphenylphosphine, thereby obtaining Ligand (6) (0.1469 g, 62.43%).

$^1$H NMR (500 MHz, CDCl$_3$) δ 7.25 (m, 16H, aromatics), 6.99 (m, 4H, aromatics, =CH—), 2.13 (m, 2H, —CH$_2$—), 1.26 (m, 2H, —CH$_2$—), 1.10 (m, 2H, —CH$_2$—), 0.70 (t, 3H, —CH$_3$); $^{13}$C NMR (600 MHz, CDCl$_3$) δ 165.2, 155.5, 140.1, 139.3, 134.9, 134.0, 133.3, 130.5, 128.2, 124.0, 115.3, 37.0, 30.9, 22.4, 13.7; $^{19}$F NMR (500 MHz, CDCl$_3$) δ -102.3; $^{31}$P NMR (500 MHz, CDCl$_3$) δ -19.2, -26.2; FT-ICR MS: m/z [M.]$^+$ calcd for C$_{30}$H$_{29}$FP$_2$: 470.1729; found: 470.1721.

[Preparation Example 7] Preparation of Ligand (7)

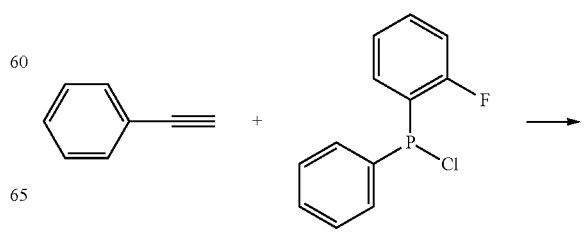

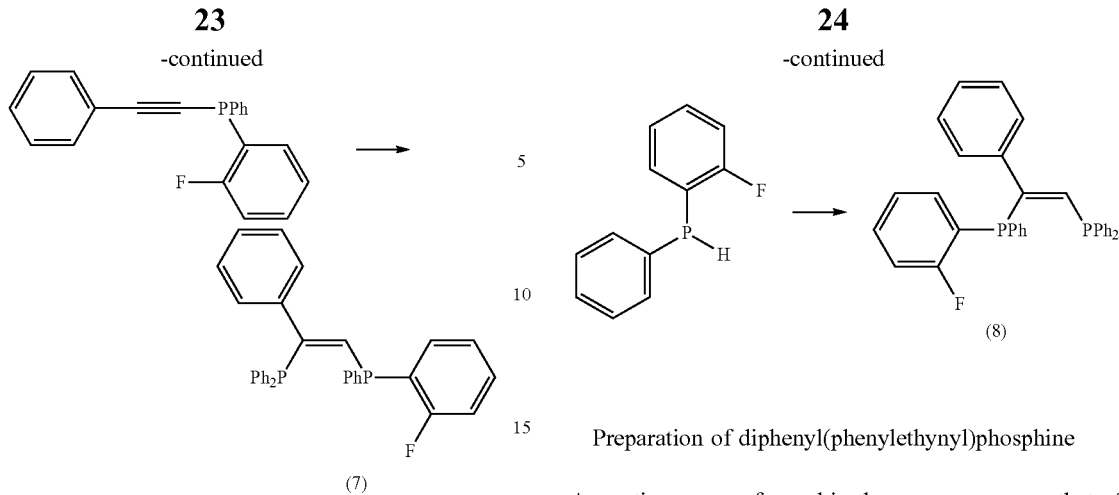

(7)

Preparation of (2-fluorophenyl)(phenyl)(phenylethynyl)phosphine

A reaction was performed in the same manner as that of the preparation method of Ligand (1) except that ethynylbenzene was used as a starting material instead of 3,3-dimethyl-1-butyne, thereby obtaining a title compound (70.95%).

$^1$H NMR (500 MHz, CDCl$_3$) δ 7.72 (m, 3H, aromatics), 7.54 (m, 2H, aromatic), 7.36 (m, 7H, aromatics), 7.17 (m, 1H, aromatics), 7.00 (m, 1H, aromatics); $^{13}$C NMR (600 MHz, CDCl$_3$) δ 165.1, 134.6, 132.8, 131.8, 129.2, 128.2, 124.5, 122.5, 115.4, 108.6, 84.2; $^{19}$F NMR (500 MHz, CDCl$_3$) δ −105.1; $^{31}$P NMR (500 MHz, CDCl$_3$) δ −45.9; FT-ICR MS: m/z [M+H]$^+$ calcd for C$_{20}$H$_{15}$FP$^+$: 305.0895; found: 305.0894.

Preparation of Ligand (7)

A reaction was performed in the same manner as that of the preparation method of Ligand (1) except that (2-fluorophenyl)(phenyl)(phenylethynyl)phosphine was used as a starting material instead of (3,3-dimethyl-1-butynyl)(2-fluorophenyl)phenylphosphine, thereby obtaining Ligand (7) (97.13%).

$^1$H NMR (500 MHz, CDCl$_3$) δ 7.40-6.90 (m, 25H, aromatics, =CH—); $^{13}$C NMR (600 MHz, CDCl$_3$) δ 165.2, 155.7, 145.9, 142.3, 139.1, 135.8, 133.3, 128.3, 126.8, 115.6; $^{19}$F NMR (500 MHz, CDCl$_3$) δ −102.3; $^{31}$P NMR (500 MHz, CDCl$_3$) δ −4.9, −25.9; FT-ICR MS: m/z [M.]$^+$ calcd for C$_{32}$H$_{25}$FP$_2$: 490.1416; found: 490.1418.

[Preparation Example 8] Preparation of Ligand (8)

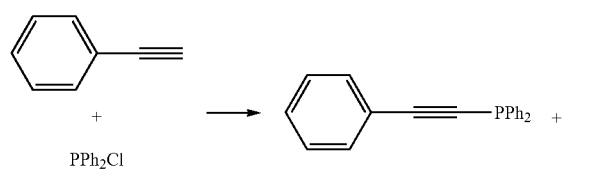

(8)

Preparation of diphenyl(phenylethynyl)phosphine

A reaction was performed in the same manner as that of the preparation method of Ligand (3) except that ethynylbenzene was used as a starting material instead of 3-methyl-1-butyne, thereby obtaining a title compound (7.865 g, 92.29%).

$^1$H NMR (500 MHz, CDCl$_3$) δ 7.68 (m, 4H, aromatics), 7.54 (m, 2H, aromatic), 7.35 (m, 9H, aromatics); $^{13}$C NMR (600 MHz, CDCl$_3$) δ 136.3, 132.6, 131.8, 128.9, 128.5, 122.7, 107.7, 85.8; $^{31}$P NMR (500 MHz, CDCl$_3$) δ −33.4; FT-ICR MS: m/z [M+H]$^+$ calcd for C$_{20}$H$_{16}$P$^+$: 287.0990; found: 287.0987.

Preparation of Ligand (8)

A reaction was performed in the same manner as that of the preparation method of Ligand (3) except that the diphenyl(phenylethynyl)phosphine prepared above was used as a starting material instead of (3-methyl-1-butynyl)diphenylphosphine, thereby obtaining Ligand (8) (0.2113 g, 86.16%).

$^1$H NMR (500 MHz, CDCl$_3$) δ 7.40-6.79 (m, 25H, aromatics, =CH—); $^{13}$C NMR (600 MHz, CDCl$_3$) δ 165.3, 154.8, 145.3, 142.1, 138.5, 133.4, 132.5, 128.3, 123.8, 114.9; $^{19}$F NMR (500 MHz, CDCl$_3$) δ −102.2; $^{31}$P NMR (500 MHz, CDCl$_3$) δ −25.9; FT-ICR MS: m/z [M.]$^+$ calcd for C$_{32}$H$_{25}$FP$_2$: 490.1416; found: 490.1415.

[Preparation Example 9] Preparation of Ligand (9)

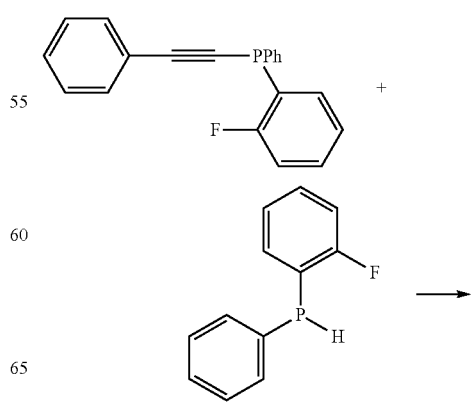

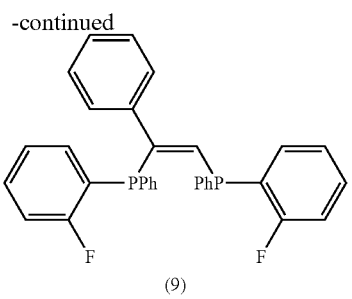
(9)

A reaction was performed in the same manner as that of the preparation method of Ligand (3) except that (2-fluorophenyl)(phenyl)(phenylethynyl)phosphine was used as a starting material instead of (3-methyl-1-butynyl)diphenylphosphine, thereby obtaining Ligand (9) (0.244 g, 99.9%).

$^1$H NMR (500 MHz, CDCl$_3$) δ 7.42-6.77 (m, 24H, aromatics); $^{13}$C NMR (600 MHz, CDCl$_3$) δ 165.4, 154.9, 143.9, 142.1, 137.9, 133.5, 132.5, 130.5, 128.5, 127.9, 125.1, 124.2, 115.7, 124.2, 115.7, 114.8; $^{19}$F NMR (500 MHz, CDCl$_3$) δ −102.2; $^{31}$P NMR (500 MHz, CDCl$_3$) δ −16.8, −35.0; FT-ICR MS: m/z [M.]$^+$ calcd for C$_{32}$H$_{24}$F$_2$P$_2$: 508.1321; found: 508.1322.

Preparation of Catalyst and Ethylene Oligomerization Reaction

Example 1

Chromium (III) chloride tris-tetrahydrofuran (CrCl$_3$(THF)$_3$) (237 mg, 0.63 µmol) was dissolved in dichloromethane (2.0 mL), and then Ligand (1) (Preparation Example 1) (298 mg, 0.63 µmol) dissolved in dichloromethane (1.0 mL) was slowly added thereto. The reaction mixture was additionally stirred for 1 hour, and then filtered using a syringe filter of 0.45 µm. The filtered liquid was treated in vacuo to remove volatile substances, thereby obtaining a dried blue solid (390 mg, 97.9%), which was referred to as Oligomerization Catalyst I.

In addition, a 2.1 L autoclave reactor was washed with nitrogen in a vacuum, 1.0 L of methylcyclohexane and 1.0 mL of mMAO-3A (7 wt %-Al) commercially available from Akzo Nobel N.V. were added thereto, and then the mixture was stirred at a stirring rate of 500 rpm. 1.9 mg of Oligomerization Catalyst I (3 µmol) prepared above was added and dispersed in 10 mL of methylcyclohexane in a 20 mL vial in a glove box, and then the mixture was added to the autoclave reactor. An oligomerization reaction was started after the temperature in the autoclave reactor was increased to 100° C. and the autoclave reactor was charged with 30 bar of ethylene. In order to control reaction heat, the reactor was cooled with an internal cooling coil to constantly maintain the temperature of 100° C. during operation. After 60 minutes, ethylene feeding to the reactor was stopped, the reaction was stopped by stopping the stirring, the excess ethylene in the reactor was discharged, and then the reactor was cooled to 10° C. or lower. The reaction product was discharged to a discharge container containing 1.5 mL of 2-ethylhexane, a small amount of organic layer sample was passed through a micron syringe filter, and then analysis was performed with GC-FID. The remaining organic layer was filtered to separate a solid wax/polymer product. These solid products were dried overnight in an oven of 100° C., and then the thus-obtained product was weighed. After GC analysis was performed, the distribution of the products of the present examples is summarized in Table 1.

Example 2

Catalyst II was prepared in the same manner as that of Example 1 except that Ligand (2) was used instead of Ligand (1), and then the oligomerization reaction was performed in the same manner as that of Example 1. The distribution of the products of the present example is summarized in Table 1.

Example 3

Catalyst III was prepared in the same manner as that of Example 1 except that Ligand (3) was used instead of Ligand (1), and then the oligomerization reaction was performed in the same manner as that of Example 1. The distribution of the products of the present example is summarized in Table 1.

Example 4

Catalyst IV was prepared in the same manner as that of Example 1 except that Ligand (4) was used instead of Ligand (1), and then the oligomerization reaction was performed in the same manner as that of Example 1. The distribution of the products of the present example is summarized in Table 1.

Example 5

Catalyst V was prepared in the same manner as that of Example 1 except that Ligand (5) was used instead of Ligand (1), and then the oligomerization reaction was performed in the same manner as that of Example 1. The distribution of the products of the present example is summarized in Table 1.

Example 6

Catalyst VI was prepared in the same manner as that of Example 1 except that Ligand (6) was used instead of Ligand (1), and then the oligomerization reaction was performed in the same manner as that of Example 1. The distribution of the products of the present example is summarized in Table 1.

Example 7

Catalyst VII was prepared in the same manner as that of Example 1 except that Ligand (7) was used instead of Ligand (1), and then the oligomerization reaction was performed in the same manner as that of Example 1. The distribution of the products of the present example is summarized in Table 1.

Example 8

Catalyst VIII was prepared in the same manner as that of Example 1 except that Ligand (8) was used instead of Ligand (1), and then the oligomerization reaction was performed in the same manner as that of Example 1. The distribution of the products of the present example is summarized in Table 1.

Example 9

Catalyst IX was prepared in the same manner as that of Example 1 except that Ligand (9) was used instead of Ligand (1), and then the oligomerization reaction was performed in the same manner as that of Example 1. The distribution of the products of the present example is summarized in Table 1.

Comparative Example 1

Catalyst A was prepared in the same manner as that of Example 1 except that Ligand (A) having the following structure was used instead of Ligand (1), and then the oligomerization reaction was performed in the same manner as that of Example 1. The distribution of the products of the present comparative example is summarized in Table 1.

Comparative Example 2

Catalyst B was prepared in the same manner as that of Example 1 except that Ligand (B) having the following structure was used instead of Ligand (1), and then the oligomerization reaction was performed in the same manner as that of Example 1. The distribution of the products of the present comparative example is summarized in Table 1.

Comparative Example 3

Catalyst C was prepared in the same manner as that of Example 1 except that Ligand (C) having the following structure was used instead of Ligand (1), and then the oligomerization reaction was performed in the same manner as that of Example 1. The distribution of the products of the present comparative example is summarized in Table 1.

Comparative Example 4

Catalyst D was prepared in the same manner as that of Example 1 except that Ligand (D) having the following structure was used instead of Ligand (1), and then the oligomerization reaction was performed in the same manner as that of Example 1. The distribution of the products of the present comparative example is summarized in Table 1.

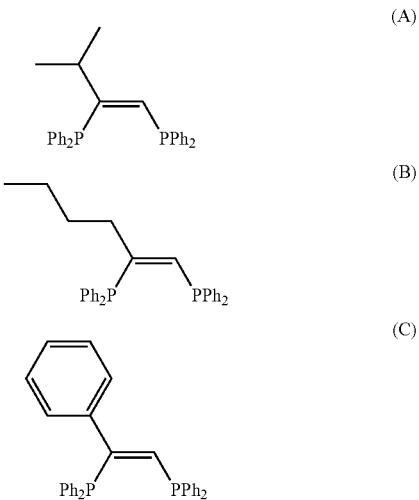

(A)

(B)

(C)

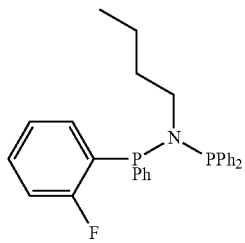

(D)

TABLE 1

|  | Total activity (kg/g-Cr/h) | C6 (wt %) | 1-Hexene in C6 (wt %) | C8 (wt %) | 1-Octene in C8 (wt %) | C10-C14 (wt %) | Polymer (wt %) |
|---|---|---|---|---|---|---|---|
| Example 1 | 1663 | 80.3 | 98.0 | 15.9 | 93.2 | 3.7 | 0.1 |
| Example 2 | 1278 | 74.4 | 95.8 | 21.7 | 94.5 | 3.5 | 0.4 |
| Example 3 | 3246 | 75.4 | 97.6 | 19.4 | 97.3 | 4.7 | 0.5 |
| Example 4 | 2914 | 84.1 | 98.6 | 11.8 | 98.0 | 3.5 | 0.6 |
| Example 5 | 1142 | 71.5 | 95.6 | 21.9 | 97.2 | 4.5 | 2.1 |
| Example 6 | 2140 | 70.2 | 96.8 | 24.9 | 83.7 | 4.0 | 0.9 |
| Example 7 | 1008 | 72.2 | 94.9 | 23.3 | 93.6 | 3.8 | 0.7 |
| Example 8 | 2068 | 75.9 | 96.7 | 19.6 | 95.5 | 4.1 | 0.4 |
| Example 9 | 1875 | 82.2 | 98.3 | 11.4 | 94.5 | 4.2 | 2.2 |
| Comparative Example 1 | 1156 | 57.7 | 88.8 | 37.9 | 96.7 | 3.9 | 0.5 |
| Comparative Example 2 | 523 | 54.9 | 91.1 | 37.1 | 95.1 | 4.3 | 3.7 |
| Comparative Example 3 | 386 | 57.0 | 86.0 | 39.6 | 96.8 | 2.5 | 0.9 |
| Comparative Example 4 | 335 | 48.9 | 92.2 | 47.6 | 95.6 | 2.3 | 1.2 |

It may be appreciated from the results of Table 1 that, when the oligomerization catalyst of the present invention was used in the oligomerization reaction of ethylene, very excellent activity was exhibited at a high temperature as compared in the comparative examples, because the oligomerization catalyst of the present invention comprises a ligand which is bis(diphenylphosphino)ethene having an asymmetric structure in which fluorine is substituted at the ortho position of phenyl bonded to a phosphorus atom, and one carbon atom is substituted with a hydrocarbyl group other than hydrogen.

In particular, in the case where the oligomerization catalyst of the present invention was used, 3.04 times or more catalytic activity was exhibited at a high temperature as compared to catalytic activity of the catalyst of Comparative Example 4 comprising a PNP ligand in which fluorine is substituted at the ortho position of phenyl bonded to a phosphorus atom.

In the case where the oligomerization catalyst of the present invention is used, catalytic activity is maintained even at a high temperature, plugging and fouling do not occur due to a small production of by-products, such that shutting down for solving the plugging and fouling is not required in a polymerization process, which is very cost-effective.

Furthermore, in the case where the oligomerization catalyst of the present invention is used, catalytic activity is very excellent even at a high temperature, such that an oligomer may be produced even in a case where small amounts of catalyst and cocatalyst are used in an oligomerization process of olefin. In addition, activity is not reduced and selectivity is also excellent even at a high temperature, such that 1-hexene or 1-octene may be produced from ethylene with high selectivity.

As described above, though the exemplary embodiments of the present invention have been described in detail, those skilled in the art may make various variations of the present invention without departing from the spirit and the scope of the present invention, as defined in the claims which follow. Accordingly, future modification of the examples of the present invention is also included in the protection scope of the present invention.

INDUSTRIAL APPLICABILITY

The oligomerization catalyst according to the present invention comprises a ligand of Formula 1 which is bis(diphenylphosphino)ethene having an asymmetric structure in which phenyl bonded to a phosphorus atom is substituted with at least one fluorine, and one carbon atom is substituted with substituted or unsubstituted hydrocarbyl other than hydrogen, such that when the oligomerization catalyst according to the present invention is used, catalytic activity and selectivity are excellent even at a high temperature during the oligomerization of ethylene.

In particular, in a case where fluorine is attached to the ortho position of phenyl in the ligand of Formula 1, catalytic activity and selectivity are excellent at a high temperature during oligomerization of ethylene.

Further, when the oligomerization catalyst of the present invention is used, catalytic activity is excellent even at a high temperature, and fouling and plugging caused by a polymer which is a by-product when an oligomer is mass-produced do not occur, such that shutting down is not required, which is very cost-efficient.

Further, when the method for producing an oligomer of the present invention is used, the oligomer may be produced with high activity and high selectivity even at a high temperature, and fouling and plugging do not occur, such that olefin may be produced through a very efficient process.

The invention claimed is:

1. A ligand represented by the following Formula 1,

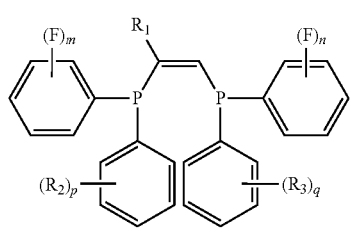

[Formula 1]

in Formula 1,

R$_1$ is substituted or unsubstituted hydrocarbyl;

R$_2$ and R$_3$ are each independently hydrocarbyl;

p and q are each independently an integer of 0 to 5; and m and n are each independently an integer of 0 to 5, where 1≤m+n≤10.

2. The ligand of claim 1, wherein the ligand is represented by the following Formula 2,

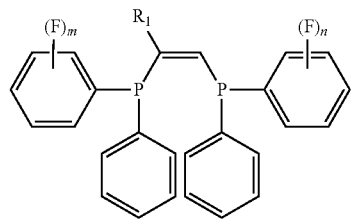

[Formula 2]

in Formula 2, R$_1$, m, and n are defined as in Formula 1 of claim 1.

3. The ligand of claim 1, wherein the ligand is represented by the following Formula 3, 4, or 5,

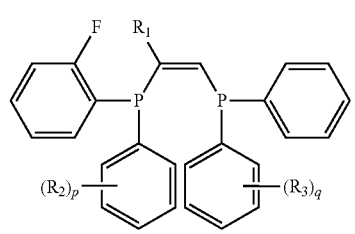

[Formula 3]

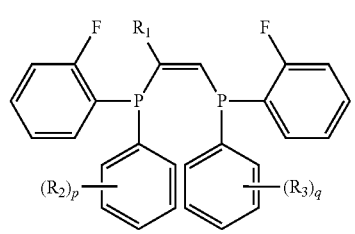

[Formula 4]

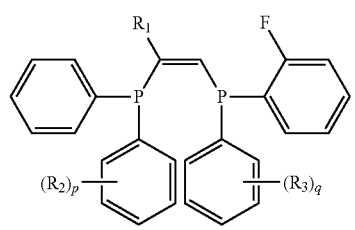

[Formula 5]

in Formulas 3 to 5, R$_1$, R$_2$, R$_3$, p, and q are defined as in Formula 1 of claim 1.

4. The ligand of claim 3, wherein R$_1$ is C1-C7alkyl or C6-C12aryl.

5. An ethylene oligomerization catalyst comprising:
the ligand of claim 1; and
a transition metal.

6. The ethylene oligomerization catalyst of claim 5, wherein the ethylene oligomerization catalyst is mononuclear or binuclear.

7. The ethylene oligomerization catalyst of claim 5, wherein the transition metal is a Group 4, Group 5, or Group 6 transition metal.

8. The ethylene oligomerization catalyst of claim 7, wherein the transition metal is chromium, molybdenum, tungsten, titanium, tantalum, vanadium, or zirconium.

9. The ethylene oligomerization catalyst of claim 8, wherein the transition metal is chromium.

10. A method for producing an ethylene oligomer, comprising contacting a catalyst composition including the ethylene oligomerization catalyst of claim 5 with ethylene.

11. The method of claim 10, wherein the catalyst composition further includes a cocatalyst.

12. The method of claim 11, wherein the cocatalyst is an organoaluminum compound, organoaluminoxane, an organoboron compound, an organic salt, or a mixture thereof.

13. The method of claim 12, wherein the cocatalyst is one or a mixture of two or more selected from the group consisting of methylaluminoxane (MAO), modified methylaluminoxane (mMAO), ethyl aluminoxane (EAO), tetraisobutyl aluminoxane (TIBAO), isobutyl aluminoxane (IBAO), trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride.

14. The method of claim 13, wherein the ethylene oligomer is 1-hexene or 1-octene.

15. The method of claim 10, wherein an aliphatic hydrocarbon is used as a reaction solvent.

16. The method of claim 15, wherein the aliphatic hydrocarbon is at least one selected from hexane, heptane, octane, nonane, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane.

* * * * *